United States Patent [19]

Kawashima

[11] Patent Number: 4,945,894
[45] Date of Patent: Aug. 7, 1990

[54] ENDOSCOPE HAVING X-RAY NON-TRANSMITTING MATERIAL

[75] Inventor: Masahiro Kawashima, Hino, Japan

[73] Assignee: Olympus Optical Co., Ltd., Tokyo, Japan

[21] Appl. No.: 416,647

[22] Filed: Oct. 3, 1989

[30] Foreign Application Priority Data

Oct. 18, 1988 [JP] Japan .................. 63-136045

[51] Int. Cl.$^5$ .............................................. A61B 1/06
[52] U.S. Cl. .......................................... 128/6; 128/658
[58] Field of Search ............... 128/4, 6, 7, 656, 658

[56] References Cited

U.S. PATENT DOCUMENTS

| | | | |
|---|---|---|---|
| 3,608,555 | 9/1971 | Greyson | 128/658 |
| 4,027,659 | 6/1977 | Slingluff | 128/658 |
| 4,657,024 | 4/1987 | Coneys | 128/658 |
| 4,790,295 | 12/1988 | Tashiro | 128/6 |

FOREIGN PATENT DOCUMENTS 61-20009  9/1986  Japan.
61-143121 9/1986  Japan.
61-203717 12/1986 Japan.

Primary Examiner—William H. Grieb
Attorney, Agent, or Firm—Frishauf, Holtz, Goodman & Woodward

[57] ABSTRACT

An endoscope has an insertion portion to be inserted in a body cavity. Image guide fibers, light guide fibers, and an objective lens are arranged in an outer tube of the insertion portion. An X-ray non-tranmitting material is mixed in an adhesive for adhering the objective lens arranged at the distal ends of the image guide fibers, and/or a coating agent for covering the image guide fibers and the light guide fibers. When the insertion portion is inserted in a body cavity, the presence of the X-ray non-transmitting material can be confirmed by an external X-ray imaging operation, and the position of the insertion portion of the endoscope can be confirmed.

11 Claims, 2 Drawing Sheets

ENDOSCOPE HAVING X-RAY NON-TRANSMITTING MATERIAL

BACKGROUND OF THE INVENTION

1. Field of the Invention

The present invention relates to an endoscope having a small diameter, which is inserted in a blood vessel of a living body to observe its interior.

2. Description of the Related Art

An insertion portion of an endoscope which is inserted in a stomach, intestinum duodenum, or large intestine to observe its interior is constituted by a flexible tube portion, a bending tube portion, and a distal-end constituting portion. Upon operation of a bending operation knob provided at an operation portion, a pulling wire inserted through the insertion portion in the vertical and lateral directions is moved forward/backward, thereby bending the bending tube portion in a desired direction. Thus, the distal-end constituting portion can be inserted in a desired direction into a body cavity. Therefore, in the flexible tube portion, an outer tube made of a synthetic resin covers the outer surface of a metal flexible tube through a blade. In the bending tube portion, an outer tube made of a synthetic resin covers the outer surfaces of metal bending bridges through a blade. Image guide fibers, light guide fibers, an insertion channel, and the like are arranged inside the insertion portion.

The insertion portion of the endoscope incorporates the metal flexible tube and blade, i.e., members which do not transmit X-rays. Therefore, when the insertion portion is inserted in a body cavity and the interior of the body cavity is observed, if an X-ray imaging operation is performed by an external X-ray apparatus, the distal end position of the insertion portion can be confirmed.

However, the diameter of an insertion portion of an endoscope which is inserted in a very narrow internal cavity such as a blood vessel must be decreased as much as possible.

The insertion portion of the endoscope which is inserted in a very narrow internal cavity such as a blood vessel is constituted as disclosed in Published Unexamined Japanese Utility Model Application No. 61-203717 or as shown in FIGS. 5 to 7. More specifically, an endoscope main body 1 is constituted by an operation portion 2 and an insertion portion 3 to be inserted in a very narrow internal cavity such as a blood vessel. The outer surface of the insertion portion 3 is covered with an outer tube 4 made of a synthetic resin material. The outer tube 4 incorporates image guide fibers 5 and light guide fibers 6. An objective lens 7 is coupled to the distal end faces of the image guide fibers 5 through a metal lens frame 8.

In the endoscope with the above structure, the image guide fibers 5 and the objective lens 7 are coupled to each other through the metal lens frame 8 which does not transmit X-rays. When the insertion portion 3 is inserted in a body cavity and its interior is observed, if an X-ray imaging operation is performed by an external X-ray apparatus, the distal end position of the insertion portion 3 can be easily confirmed. However, when the lens frame 8 is used, a decrease in diameter of the insertion portion 3 is limited.

In order to eliminate this drawback, Published Unexamined Japanese Utility Model Application No. 61-143121 discloses a structure in which the lens frame 8 is omitted, and the diameter of the endoscope is further decreased. However, the image guide fibers 5, the light guide fibers 6, and the objective lens 7 of such a small-diameter endoscope are formed of glass which transmits X-rays. Since the lens frame 8 is omitted, there are no metal constituting elements, i.e., no members which do not transmit X-rays in the insertion portion 3. Therefore, even if the distal end position of the insertion portion 3 is to be confirmed by external X-ray imaging operation, it is impossible to do so.

An endoscope in which the image guide fibers 5 are covered with a coating layer 9, as shown in FIG. 5, is known as per Published Unexamined Japanese Patent Application No. 61-20009. Since the coating layer 9 is formed of a silicone resin which transmits X-rays, the position of the distal end portion of the insertion portion 3 cannot be confirmed.

U.S. Pat. No. 3,608,555 discloses a catheter in which an X-ray non-transmitting material is mixed in a synthetic resin tube. However, most of the X-ray non-transmitting materials include heavy metals. Therefore, if such a material containing a heavy metal is mixed in a portion which is brought into direct contact with a body fluid, this poses problems of affinity and noxiousness to a living body. Therefore, the synthetic resin tube cannot be employed as the outer tube of the insertion portion of the endoscope.

U.S. Pat. No. 4,027,659 discloses a medical tube in which an X-ray non-transmitting material is partially mixed along the longitudinal direction. This tube also poses the problems of affinity and noxiousness to a living body like in U.S. Pat. No. 3,608,555.

As described above, when the lens frame or the like is omitted to decrease the diameter of the insertion portion of the endoscope to be inserted in a blood vessel or the like, there are no X-ray non-transmitting materials in the insertion portion, and the position of the insertion portion cannot be confirmed by the external X-ray imaging operation. If a heavy metal material is mixed in the outer tube, the adverse influence on a living body is expected.

SUMMARY OF THE INVENTION

It is an object of the present invention to provide an endoscope in which the diameter of an insertion portion can be decreased, and when the insertion portion is inserted in a body cavity and its interior is observed by an external X-ray imaging operation, the distal end position of the insertion portion can be easily confirmed, and which is free from the adverse influence on a living body.

According to the present invention, there is provided an endoscope comprising: an endoscope main body having an insertion portion to be inserted in a body cavity, the insertion portion comprising an outer tube, and at least image guide fibers, light guide fibers disposed at the distal ends of the image guide fibers, and an objective lens which are disposed in the outer tube; an adhesive for adhering the objective lens to the outer tube; a coupling agent for binding and coupling at least distal end portions of the light guide fibers; and an X-ray non-transmitting material mixed in at least one of the adhesive and the coupling agent.

According to the present invention, when the insertion portion is inserted in a body cavity and when X-rays are radiated from an external X-ray apparatus during observation of the interior of a body cavity, the position of the X-ray non-transmitting material mixed in the adhesive for adhering the objective lens to the outer tube of the insertion portion or in the coupling agent for binding and coupling the light guide fibers, i.e., the position of the distal end portion of the insertion portion can be confirmed.

According to the present invention, there is provided an endoscope comprising: an endoscope main body having an insertion portion to be inserted in a body cavity, the insertion portion comprising an outer tube, and at least image guide fibers, light guide fibers, and an objective lens which are disposed in the outer tube; a filler filled between the outer surfaces of the image guide fibers and the light guide fibers and the outer tube; and an X-ray non-transmitting material mixed in the filler.

According to the present invention, when the insertion portion is inserted in a body cavity and when X-rays are radiated from an external X-ray apparatus during observation of the interior of a body cavity, the position of the X-ray non-transmitting material mixed in the filler filled in a space inside the outer tube of the insertion portion, i.e., the position of the distal end portion of the insertion portion can be confirmed.

The outer tube is formed of an X-ray transmitting material such as ethylene tetrafluoride, PVC, polyurethane, or the like.

The X-ray non-transmitting material is barium sulfate or bismuth oxide.

DETAILED DESCRIPTION OF THE PREFERRED EMBODIMENTS

Preferred embodiments of the present invention will now be described with reference to the accompanying drawings.

Figure 1:
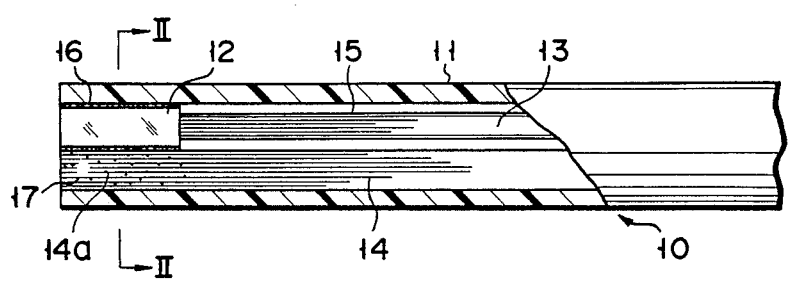
FIG. 1 is a longitudinal sectional view of an insertion portion of a small-diameter endoscope according to the first embodiment of the present invention.
Figure 2:
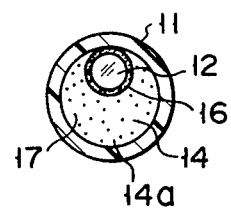
FIG. 2 is a sectional view taken along a line II—II in FIG. 1.

FIGS. 1 and 2 show the first embodiment of the present invention. FIGS. 1 and 2 show an insertion portion 10 of a small-diameter endoscope which is inserted in a blood vessel of a living body to observe its interior. An outer tube 11 of the insertion portion 10 is formed of an X-ray transmitting material such as ethylene tetrafluoride, polyvinyl chloride, polyurethane, or the like which is free from an adverse influence on a living body. An objective lens 12 for forming an object image is provided at the distal end portion of the outer tube 11. Image guide fibers 13 for transmitting the formed image and light guide fibers 14 for transmitting light for illuminating an object are arranged in the outer tube 11. The outer surfaces of the image guide fibers 13 are covered with a coating agent, e.g., an image guide fiber jacket 15, such as silicone containing an X-ray non-transmitting material, e.g., barium sulfate or bismuth oxide. The objective lens 12 and the distal ends of the image guide fibers 13 are fixed by a transparent adhesive. The side surface of the objective lens 12 is adhered to the inner surface of the outer tube 11 by a light non-transmitting adhesive 16. Distal end portions 14a of the light guide fibers 14 are fixed to each other by a coupling agent 17 such as an adhesive or filler and are also fixed to the outer tube 11 by an adhesive. Thus, the distal end portions 14a are held in a watertight and airtight state.

According to the insertion portion 10 of the endoscope with this structure, the objective lens 12 and the distal end faces of the image guide fibers 13 arranged in the outer tube 11 are fixed to each other by a transparent adhesive, and no conventional lens frame is required. Therefore, the outer diameter of the insertion portion 10 can be decreased as much as possible, thus obtaining a small-diameter endoscope capable of being inserted in a blood vessel or the like. In addition, when X-rays are radiated on the insertion portion 10 through a body in order to externally confirm the position of the insertion portion 10 inserted in a body cavity, since the outer tube 11, the objective lens 12, the image guide fibers 13, and the light guide fibers 14 are formed of an X-ray transmitting material, the position of the insertion portion 10 cannot be confirmed. However, since the image guide fiber jacket 15 coated on the image guide fibers 13 is formed of an X-ray non-transmitting material, the position of the insertion portion 10 can be confirmed. Therefore, the endoscope can be operated while confirming the position of the insertion portion 10 of the endoscope.

In the first embodiment, the image guide fiber jacket 15 is formed of a coating agent containing an X-ray non-transmitting material. However, the X-ray non-transmitting material such as barium may be mixed in the coupling agent 17 such as an adhesive or filler for adhering the distal end portions 14a of the light guide fibers 14. With this structure, the X-ray non-transmitting material is present in the distal end portion of the insertion portion 10 and the position of the distal end can be accurately confirmed. In addition, the X-ray non-transmitting material provides an increased thickness in an X-ray radiation direction, thus improving contrast characteristics.

When the X-ray non-transmitting material is mixed in the adhesive 16 applied on the side surface of the objective lens 12, the same effect as in the first embodiment can be obtained. According to this embodiment, the adhesive is brought in direct contact with a body fluid, and the X-ray non-transmitting material mixed in the adhesive 16 may be mixed in the body fluid. However, since a contact area is much smaller than in the prior art, the X-ray non-transmitting material does not adversely influence a living body.

Figure 3:
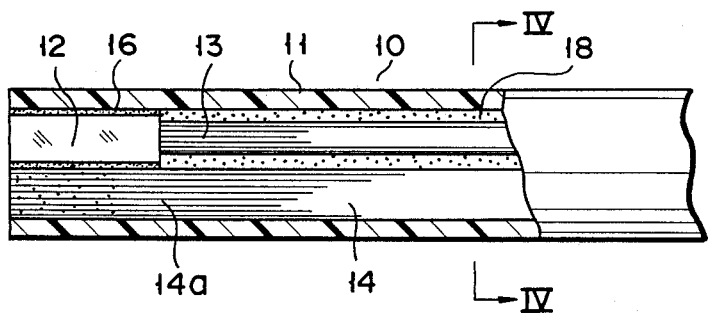
FIG. 3 is a longitudinal sectional view of an insertion portion of a small-diameter endoscope according to the second embodiment of the present invention.
Figure 4:
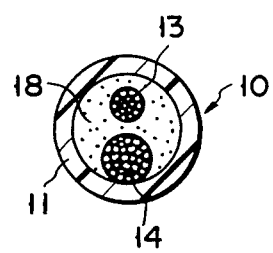
FIG. 4 is a sectional view taken along a line IV—IV in FIG. 3.
Figure 5:
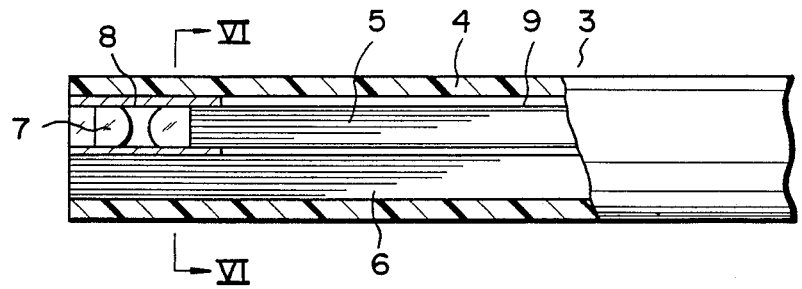
FIG. 5 is a longitudinal sectional view of an insertion portion of a conventional small-diameter endoscope.
Figure 6:
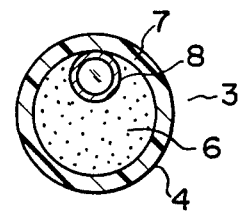
FIG. 6 is a sectional view taken along a line VI—VI in FIG. 5.
Figure 7:
FIG. 7 is a side view showing the overall structure of the conventional small-diameter endoscope.

FIGS. 3 and 4 show the second embodiment of the present invention. The same reference numerals in FIGS. 3 and 4 denote the same parts as in the first embodiment, and a detailed description thereof will be omitted. An outer tube 11 of an insertion portion 10 is formed of an X-ray transmitting material such as ethylene tetrafluoride, PVC, or polyurethane which has a less influence on a living body. An objective lens 12 for forming an object image, image guide fibers 13 for transmitting the formed image, and light guide fibers 14 for transmitting light for illuminating an object are arranged in the outer tube 11. The image guide fibers 13 and the light guide fibers 14 form columnar bundles. Therefore, a space is formed between the bundles and the inner surface of the outer tube 11. A filler 18 of a gel-like material mixed with an X-ray non-transmitting material, e.g., barium sulfate or bismuth oxide is filled in the space. Thus, if the insertion portion 10 is bent, the filler 18 prevents the bundles of the image guide fibers 13 and the light guide fibers 14 from being broken.

Therefore, when X-rays are radiated on the insertion portion 10 through a body in order to externally confirm the position of the insertion portion 10 inserted in a body cavity, since the outer tube 11, the objective lens 12, the image guide fibers 13, and the light guide fibers 14 are formed of an X-ray transmitting material, the position of the insertion portion 10 cannot be confirmed. However, since the filler 18 filled in the space between the outer tube 11 and the image guide fibers 13 and the light guide fibers 14 is the X-ray non-transmitting material, the position of the insertion portion 10 can be confirmed. Therefore, the endoscope can be operated while confirming the insertion portion 10 of the endoscope along its total length.

If the filler 18 mixed with the X-ray non-transmitting material is filled in only the distal end side of the insertion portion 10, only the distal end side of the insertion portion 10 can be confirmed by an X-ray imaging operation. Since the filler 18 is not externally exposed, it does not adversely influence a living body. Furthermore, the insertion portion may be modified as follows. A channel (not shown) is provided in the outer tube 11 together with the image guide fibers 13 and the light guide fibers 14, and a physiological saline solution is injected into a blood vessel to assure a field of view in the blood vessel.

What is claimed is:

1. An endoscope comprising:
    an endoscope main body having an insertion portion to be inserted in a body cavity, said insertion portion comprising an outer tube, and at least image guide fibers having distal ends, light guide fibers having distal end portions, and an objective lens which are disposed at the distal ends of said image guide fibers, said image guide fibers, said light guide fibers and said objective lens being respectively disposed in said outer tube, and said objective lens being disposed at the distal ends of said image guide fibers;
    an adhesive for adhering said objective lens to said outer tube;
    a coupling agent for binding and coupling at least said distal end portions of said light guide fibers; and
    an X-ray non-transmitting material mixed in at least one of said adhesive and said coupling agent.

2. An endoscope according to claim 1, wherein said outer tube is formed of an X-ray transmitting material selected from the group consisting of ethylene tetrafluoride, PVC, and polyurethane.

3. An endoscope according to claim 1, wherein said X-ray non-transmitting material is selected from the group consisting of barium sulfate and bismuth oxide.

4. An endoscope comprising:
    an endoscope main body having an insertion portion to be inserted in a body cavity, said insertion portion comprising an outer tube, and at least image guide fibers, light guide fibers, and an objective lens which are respectively disposed in said outer tube;
    a filler filled in a space between said image guide fibers, said light guide fibers, and said outer tube; and
    an X-ray non-transmitting material mixed in said filler.

5. An endoscope according to claim 4, wherein said X-ray non-transmitting material is selected from the group consisting of barium sulfate and bismuth oxide.

6. An endoscope according to claim 4, wherein said X-ray non-transmitting material is a gel-like material.

7. An endoscope according to claim 4, wherein said outer tube is formed of a material selected from the group consisting of ethylene tetrafluoride, PVC, and polyurethane.

8. An endoscope comprising:
    an endoscope main body having an insertion portion to be inserted in a body cavity, said insertion portion comprising an outer tube, and at least image guide fibers having distal ends, light guide fibers having distal end portions, and an objective lens which are disposed at the distal ends of said image guide fibers, said image guide fibers, said light guide fibers and said objective lens being respectively disposed in said outer tube;
    an adhesive for adhering said objective lens disposed at the distal ends of said image guide fibers to said outer tube;
    a coupling agent for binding and coupling at least said distal end portions of said light guide fibers;
    a coating agent coated on outer surfaces of said image guide fibers; and
    an X-ray non-transmitting material mixed in said coating agent.

9. An endoscope according to claim 8, wherein said outer tube is formed of an X-ray transmitting material selected from the group consisting of ethylene tetrafluoride, PVC, and polyurethane.

10. An endoscope according to claim 8, wherein said X-ray non-transmitting material is selected from the group consisting of barium sulfate and bismuth oxide.

11. An endoscope according to claim 8, wherein said coating agent comprises silicone containing barium sulfate or bismuth oxide.

* * * * *